United States Patent
Conyers et al.

(10) Patent No.: US 12,097,363 B2
(45) Date of Patent: Sep. 24, 2024

(54) CONNECTORS AND CABLES FOR USE WITH VENTRICLE ASSIST SYSTEMS

(71) Applicant: TC1 LLC, St. Paul, MN (US)

(72) Inventors: Kevin Conyers, Pleasant Hill, CA (US); Jaime Arturo Romero, San Leandro, CA (US)

(73) Assignee: TC1 LLC, St. Paul, MN (US)

( * ) Notice: Subject to any disclaimer, the term of this patent is extended or adjusted under 35 U.S.C. 154(b) by 1084 days.

(21) Appl. No.: 16/987,535

(22) Filed: Aug. 7, 2020

(65) Prior Publication Data
US 2020/0360584 A1 Nov. 19, 2020

Related U.S. Application Data (63) Continuation of application No. 15/980,441, filed on May 15, 2018, now Pat. No. 10,773,004, which is a
(Continued)

(51) Int. Cl.
*A61M 60/148* (2021.01)
*A61M 60/183* (2021.01)
(Continued)

(52) U.S. Cl.
CPC ........ *A61M 60/148* (2021.01); *A61M 60/183* (2021.01); *A61M 60/508* (2021.01);
(Continued)

(58) Field of Classification Search
CPC .............. A61M 60/148; A61M 60/178; A61M 60/183; A61M 60/232; A61M 60/508;
(Continued)

(56) References Cited

U.S. PATENT DOCUMENTS

| 3,882,861 A | 5/1975 | Kettering et al. |
| 4,521,871 A | 6/1985 | Galdun et al. |

(Continued)

FOREIGN PATENT DOCUMENTS

| EP | 1 812 094 | 5/2006 |
| WO | 2006/055745 | 5/2006 |

(Continued)

OTHER PUBLICATIONS

"Berlin Heart Incor", My LVAD, Available online at: http://www.mylvad.com/content/berlin-heart-incor, Jul. 16, 2015, 3 pages.
(Continued)

*Primary Examiner* — Matthew W Schall
(74) *Attorney, Agent, or Firm* — Kilpatrick Townsend & Stockton LLP (57) ABSTRACT

Systems, assemblies, and related modules for connecting components of medical devices employ connector cables with electrical conductors and optical fibers. A connector assembly for coupling a battery module with a medical system including an implanted or worn medical device includes an input connector and an output connector. The input connector includes metal contact plates, has no moving parts, and is sealed to prevent water or dust ingression into the housing. The output connector includes metal pins to electrically couple to the metal plates of the input connector, a connector cable including electrical conductors coupled to the metal pins configured to transmit electrical power and an optical fiber configured to transmit data, and a latching mechanism disposed at an end of the output connector configured to physically attach the output connector to the housing. The cable body has a substantially flat cross-section.

20 Claims, 5 Drawing Sheets

Related U.S. Application Data continuation of application No. PCT/US2016/062619, filed on Nov. 17, 2016.

(60) Provisional application No. 62/258,292, filed on Nov. 20, 2015.

(51) Int. Cl.
*A61M 60/508* (2021.01)
*A61M 60/861* (2021.01)
*A61M 60/871* (2021.01)
*A61M 60/178* (2021.01)
*A61M 60/232* (2021.01)

(52) U.S. Cl.
CPC ........ *A61M 60/861* (2021.01); *A61M 60/871* (2021.01); *A61M 60/178* (2021.01); *A61M 60/232* (2021.01)

(58) Field of Classification Search
CPC .... A61M 60/861; A61M 60/871; A61M 1/10; A61M 1/12
See application file for complete search history.

(56) References Cited

U.S. PATENT DOCUMENTS

| | | |
|---|---|---|
| 5,046,965 A | 9/1991 | Neese et al. |
| 5,282,757 A | 2/1994 | Maeda |
| 5,367,593 A | 11/1994 | Lebby et al. |
| 5,695,474 A | 12/1997 | Daugherty |
| 5,888,242 A | 3/1999 | Antaki et al. |
| 5,935,105 A | 8/1999 | Manning et al. |
| 5,991,595 A | 11/1999 | Romano et al. |
| 6,071,093 A | 6/2000 | Hart |
| 6,106,971 A | 8/2000 | Spotnitz |
| 6,116,862 A | 9/2000 | Rau et al. |
| 6,123,726 A | 9/2000 | Mori et al. |
| 6,146,179 A | 11/2000 | Denny et al. |
| 6,183,412 B1 | 2/2001 | Benkowski et al. |
| 6,234,772 B1 | 5/2001 | Wampler et al. |
| 6,264,635 B1 | 7/2001 | Wampler et al. |
| 6,494,736 B2 | 12/2002 | Mito |
| 6,592,620 B1 | 7/2003 | Lancisi et al. |
| 6,688,861 B2 | 2/2004 | Wampler |
| 7,131,860 B2 | 11/2006 | Sartor et al. |
| 7,331,793 B2 | 2/2008 | Hernandez et al. |
| 7,340,304 B2 | 3/2008 | MacDonald et al. |
| 7,425,142 B1 | 9/2008 | Putz |
| 7,658,613 B1 | 2/2010 | Griffin et al. |
| 7,699,586 B2 | 4/2010 | LaRose et al. |
| 7,961,156 B2 | 6/2011 | Knott et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,029,441 B2 | 10/2011 | Mazza et al. |
| 8,152,493 B2 | 4/2012 | LaRose et al. |
| 8,157,720 B2 | 4/2012 | Marseille et al. |
| 8,186,665 B2 | 5/2012 | Akema |
| 8,323,174 B2 | 12/2012 | Jeevanandam et al. |
| 8,344,847 B2 | 1/2013 | Moberg et al. |
| 8,348,678 B2 | 1/2013 | Hardisty et al. |
| 8,449,444 B2 | 5/2013 | Poirier |
| 8,506,471 B2 | 8/2013 | Bourque |
| 8,562,508 B2 | 10/2013 | Dague et al. |
| 8,596,881 B2 | 12/2013 | Umeno |
| 8,597,350 B2 | 12/2013 | Rudser et al. |
| 8,628,460 B2 | 1/2014 | Yomtov et al. |
| 8,639,348 B2 | 1/2014 | Geheb |
| 8,652,024 B1 | 2/2014 | Yanai et al. |
| 8,657,733 B2 | 2/2014 | Ayre et al. |
| 8,668,473 B2 | 3/2014 | LaRose et al. |
| 8,684,763 B2 | 4/2014 | Mattson et al. |
| 8,827,569 B2 | 9/2014 | Yamada |
| 8,894,561 B2 | 11/2014 | Callaway et al. |
| 8,971,958 B2 | 3/2015 | Frikart et al. |
| 9,302,035 B2 | 4/2016 | Marseille et al. |
| 10,722,633 B2 | 7/2020 | Kimball et al. |
| 2002/0007198 A1 | 1/2002 | Haupert et al. |
| 2005/0071001 A1 | 3/2005 | Jarvik |
| 2006/0214510 A1 | 9/2006 | Patel |
| 2007/0078293 A1 | 4/2007 | Shambaugh, Jr. et al. |
| 2007/0142696 A1 | 6/2007 | Crosby et al. |
| 2008/0021394 A1 | 1/2008 | LaRose et al. |
| 2009/0118827 A1 | 5/2009 | Sugiura |
| 2009/0203957 A1 | 8/2009 | LaRose et al. |
| 2011/0160516 A1 | 6/2011 | Dague et al. |
| 2011/0218383 A1 | 9/2011 | Broen et al. |
| 2012/0046514 A1 | 2/2012 | Bourque |
| 2012/0095281 A1 | 4/2012 | Reichenbach et al. |
| 2012/0157755 A1 | 6/2012 | D'ambrosio |
| 2012/0172657 A1 | 7/2012 | Marseille et al. |
| 2012/0183261 A1 | 7/2012 | Schwandt et al. |
| 2013/0096364 A1 | 4/2013 | Reichenbach et al. |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0225909 A1 | 8/2013 | Dormanen et al. |
| 2013/0314047 A1 | 11/2013 | Eagle et al. |
| 2014/0073838 A1 | 3/2014 | Dague et al. |
| 2014/0194985 A1 | 7/2014 | Vadala, Jr. |
| 2014/0243970 A1 | 8/2014 | Yanai |
| 2014/0309733 A1 | 10/2014 | Cotter et al. |
| 2015/0028797 A1 | 1/2015 | Miller et al. |
| 2015/0038771 A1 | 2/2015 | Marseille et al. |
| 2015/0120067 A1 | 4/2015 | Wing et al. |
| 2015/0290374 A1 | 10/2015 | Bourque et al. |
| 2016/0095968 A1 | 4/2016 | Rudser |
| 2018/0256796 A1 | 9/2018 | Hansen |
| 2018/0256800 A1 | 9/2018 | Conyers et al. |

FOREIGN PATENT DOCUMENTS

| | | |
|---|---|---|
| WO | 2010122139 | 10/2010 |
| WO | 2011081626 | 7/2011 |
| WO | 2014107424 | 7/2014 |
| WO | 2015017770 | 2/2015 |
| WO | 2017087380 | 5/2017 |

OTHER PUBLICATIONS

"The HeartMate II System", HeartMate II, Left Ventricular Assist System, Available online at: http://heartmateii.com/heartmate-ii-system.aspx, Jul. 16, 2015, 2 pages.

CONNECTORS AND CABLES FOR USE WITH VENTRICLE ASSIST SYSTEMS

CROSS-REFERENCE TO RELATED APPLICATION

The present application is a Continuation of U.S. patent application Ser. No. 15/980,441 filed May 15, 2018 (Allowed); which is a Continuation of PCT/US2016/062619 filed Nov. 17, 2016; which claims the benefit of priority to U.S. Provisional Appln No. 62/258,292 filed Nov. 20, 2015; the full disclosures of which are incorporated herein by reference in their entirety for all purposes.

BACKGROUND

Ventricular assist devices, known as VADs, often include an implantable blood pump and are used for both short-term (i.e., days, months) and long-term applications (i.e., years or a lifetime) when a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries and/or high blood pressure can leave a heart too weak to pump enough blood to the body. As symptoms worsen, advanced heart failure develops.

A patient suffering from heart failure may use a VAD while awaiting a heart transplant or as a long term destination therapy. A patient may also use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

Patients using a ventricular assist system (VAS) and their supporting caregivers or providers (hereinafter "users") can use non-implanted replenishable and/or replaceable power supplies to maintain mobility. Such non-implanted power supplies typically include battery packs and AC wall power converters. The power from these sources may be conveyed to the VAD via a VAS controller using cables. Many VAS include multiple externally worn components including the VAS controller, battery packs, and other components.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Embodiments described herein include connector assemblies for coupling externally worn components of medical systems including implanted or worn medical devices. The connector assemblies can include connector cables having a flat cross section, conductors for transferring electrical power, and/or an optical fiber for transmitting data. Connector cables having a flat cross section conform well with the body of a patient, thereby being more comfortable and inhibiting twisting of the connector cable. The conductors and the optical fiber can be arranged in a symmetrical linear array, thereby preventing misconnection via improper orientation. The connector assemblies can include sealed contacts that are easily cleaned without penetration of cleaning fluid into components of the medical system. A connector assembly can include a latching mechanism configured for secure connection of the connector assembly to a component of the medical system. One embodiment of the invention is directed to forming a system using any of the devices described herein.

Thus, in one aspect a connector assembly is provided for coupling a battery module with a medical system including an implanted or worn medical device. The connector assembly may include an input connector mounted to a housing. The input connector may include metal contact plates, may have no moving parts, and may be sealed to prevent water or dust ingression into the housing. The connector assembly may also include an output connector. The output connector may include metal pins of a complementary shape and size to the metal contact plates of the input connector so as to allow electrical connection between the input connector and the output connector. The metal pins may extend from a first end of the output connector. The output connector may also include a connector cable with electrical conductors and an optical fiber, the electrical conductors being coupled to the metal pins configured to transmit electrical power, the optical fiber being configured to transmit data. The connector cable may have a substantially flat cross-section. The output connector may also include a latching mechanism disposed at the first end of the output connector configured to physically attach the output connector to the housing.

In many embodiments of the assembly, the latching mechanism is a mechanical latching mechanism. In some embodiments of the assembly, the latching mechanism includes two latching arms, wherein each of the latching arms includes a dimple of a complementary shape and size to a respective recess on a surface of the housing.

In many embodiments of the assembly, the latching mechanism is a magnetic latching mechanism. In some embodiments of the assembly, the latching mechanism includes a first magnetic element configured to latch to a second magnetic element mounted to the housing. In some embodiments of the system, the first magnetic element is configured to unlatch from the second magnetic element upon application of a particular breakaway force.

In many embodiments of the assembly, the metal pins may be designed to avoid damaging the metal contact plates. In some embodiments of the assembly, the metal pins may include spring-loaded pins.

In many embodiments of the assembly, the electrical conductors and the optical fiber are arranged to allow increased flexibility. In some embodiments, the electrical conductors and the optical fiber are arranged in a linear array within the connector cable so that the connector cable has an elongated rectangular cross section. In some embodiments, the electrical conductors include two redundant pairs of conductors arranged symmetrically on opposite sides of the optical fiber to enable coupling of the output connector to the input connector in each of two opposite orientations.

In many embodiments of the assembly, the output connector includes multiple sets of metal pins disposed at opposite ends of the connector. In some embodiments, the output connector includes a second set of metal pins configured to electrically couple the output connector to a second input connector, wherein the second set of metal pins are coupled to the electrical conductors and extend from a second end of the output connector.

In many embodiments of the assembly, the input connector is part of a battery module. In some embodiments of the assembly, the housing is a first housing of a component of the medical system, and the battery module includes a second housing. In some embodiments, the connector cable is fixedly connected with the second housing.

In another aspect, a mechanical circulatory support system is provided. The system includes an implantable blood pump, an external controller configured to supply power to the implantable blood pump and including an external controller input connector, a battery module including a housing and one or more battery cells disposed within the housing, and a connector cable. The connector cable may be configured to removably couple the external controller input connector to the battery module, wherein the connector cable includes electrical conductors configured to transfer power from the one or more battery cells to the external controller and an optical fiber to transfer data between the external controller and the battery module.

In many embodiments of the system, the electrical conductors and optical fiber may be arranged to allow for flexibility. In some embodiments, the electrical conductors and the optical fiber are arranged in a linear array within the connector cable so that the connector cable has an elongated rectangular cross section. In some embodiments, the electrical conductors include two redundant pairs of conductors arranged symmetrically on opposite sides of the optical fiber to enable coupling of the battery module to the external controller input connector in each of two opposite orientations.

In many embodiments of the system, the external controller input connector may be designed without moving parts. In some embodiments, the external controller input connector includes metal contact plates, has no moving parts, and is sealed to prevent water or dust ingression into the external controller via the external controller input connector.

In many embodiments of the system, the metal pins may be designed to avoid damaging the metal contact plates. In some embodiments, the connector cable include spring-loaded metal pins of a complementary shape and size to the metal contact plates of the external controller input connector so as to allow electrical connection between the battery module and the external controller, wherein the metal pins extend from a first end of the connector cable.

In many embodiments of the system, the housing is a first housing, the external controller includes a second housing, and the connector cable includes a latching mechanism configured to physically attach the connector cable to the second housing. In some embodiments, the latching mechanism includes two latching arms, wherein each of the latching arms includes a dimple of a complementary shape and size to a respective recess on a surface of the second housing. In some embodiments, the latching mechanism includes a first magnetic element configured to latch to a second magnetic element mounted to the second housing. In some embodiments, the first magnetic element is configured to unlatch from the second magnetic element upon application of a particular breakaway force.

In many embodiments of the system, the connector cable is fixedly connected within the housing and extends from the housing to a battery module output connector, wherein the battery module output connector is configured to be removably coupled with the external controller input connector. In some embodiments, the battery module includes a spooling assembly on which the connector cable can be spooled an unspooled to vary a length by which the connector cable extends from the housing.

In many embodiments of the system, the battery module includes a battery module output connector, and the connector cable includes a first connector at a first end configured to be removably coupled with the external controller input connector and a second connector at a second end configured to be removably coupled with the battery module output connector.

In many embodiments of the system, the battery module includes connections for receiving power from another source. In some embodiments, the battery module includes a battery module input connector configured to receive electrical power from another battery module and/or a charging unit.

In another aspect, a battery module for a medical support system including an implantable or wearable medical device is provided. The battery module includes a housing, one or more battery cells disposed within the housing, a connector cable fixedly connected with the housing and extending from the housing to a distal end of the connector cable, and a battery module output connector. The battery module output connector may be connected to the distal end of the connector cable and configured to be removably coupled with a medical device input connector operatively coupled with the medical device. The connector cable may include electrical conductors and an optical fiber, the electrical conductors configured to transfer power from the one or more battery cells to the medical device via the medical device input connector, the optical fiber being configured to transfer data between the medical device and the battery module.

In many embodiments of the battery module, the electrical conductors and optical fiber may be arranged for increased flexibility. In some embodiments of the battery module, the electrical conductors and the optical fiber are arranged in a linear array within the connector cable so that the connector cable has an elongated rectangular cross section. In some embodiments of the battery module, the electrical conductors include two redundant pairs of conductors arranged symmetrically on opposite sides of the optical fiber to enable coupling of the battery module output connector to the medical device input connector in each of two opposite orientations. In many embodiments, the battery module may include a spooling assembly on which the connector cable can be spooled and unspooled to vary a length by which the connector cable extends from the housing.

In many embodiments of the battery module, the metal pins may be designed to avoid damaging portions of the medical device. In some embodiments, the battery module output connector includes spring-loaded metal pins coupled to the electrical conductors, wherein the spring-loaded metal pins are of complementary shapes and sizes to respective metal contact plates of the medical device input connector so as to allow electrical connection between the battery module and the medical device.

In many embodiments of the battery module, the battery module output connector includes a latching mechanism configured to physically attach the battery module to a medical device housing. In some embodiments of the battery module, the latching mechanism includes two latching arms, wherein each of the latching arms includes a dimple of a complementary shape and size to a respective recess on a surface of the medical device housing. In some embodiments of the battery module, the latching mechanism includes a first magnetic element configured to latch to a second magnetic element mounted to the medical device housing. In some embodiments, the first magnetic element is configured to unlatch from the second magnetic element upon application of a particular breakaway force.

In many embodiments, the battery module includes connectors to receive electrical power from alternate sources. In some embodiments, the battery module includes a battery module input connector configured to receive electrical power from another battery module and/or a charging unit.

In another aspect, a mechanical circulatory support system is provided. The system includes an implantable blood pump, an external controller configured to supply power to the implantable blood pump and including an external controller input connector, a battery module including a housing and one or more battery cells disposed within the housing, and a connector cable. The connector cable may be configured to removably couple the external controller input connector to the battery module, wherein the connector cable includes two redundant pairs of electrical conductors configured to transfer power from the one or more battery cells to the external controller and an optical fiber to transfer data between the external controller and the battery module. The two redundant pairs of electrical conductors may be arranged symmetrically on opposite sides of the optical fiber to enable coupling of the battery module to the external controller input connector in each of two opposite orientations.

In many embodiments of the system, the electrical conductors and optical fiber may be arranged to allow for flexibility. In some embodiments, the electrical conductors and the optical fiber are arranged in a linear array within the connector cable so that the connector cable has an elongated rectangular cross section.

In many embodiments of the system, the external controller input connector may be designed without moving parts. In some embodiments, the external controller input connector includes metal contact plates, has no moving parts, and is sealed to prevent water or dust ingression into the external controller via the external controller input connector.

In many embodiments of the system, the metal pins may be designed to avoid damaging the metal contact plates. In some embodiments, the connector cable include spring-loaded metal pins of a complementary shape and size to the metal contact plates of the external controller input connector so as to allow electrical connection between the battery module and the external controller, wherein the metal pins extend from a first end of the connector cable.

In many embodiments of the system, the housing is a first housing, the external controller includes a second housing, and the connector cable includes a latching mechanism configured to physically attach the connector cable to the second housing. In some embodiments, the latching mechanism includes two latching arms, wherein each of the latching arms includes a dimple of a complementary shape and size to a respective recess on a surface of the second housing. In some embodiments, the latching mechanism includes a first magnetic element configured to latch to a second magnetic element mounted to the second housing. In some embodiments, the first magnetic element is configured to unlatch from the second magnetic element upon application of a particular breakaway force.

In many embodiments of the system, the connector cable is fixedly connected within the housing and extends from the housing to a battery module output connector, wherein the battery module output connector is configured to be removably coupled with the external controller input connector. In some embodiments, the battery module includes a spooling assembly on which the connector cable can be spooled an unspooled to vary a length by which the connector cable extends from the housing.

In many embodiments of the system, the battery module includes a battery module output connector, and the connector cable includes a first connector at a first end configured to be removably coupled with the external controller input connector and a second connector at a second end configured to be removably coupled with the battery module output connector.

In many embodiments of the system, the battery module includes connections for receiving power from another source. In some embodiments, the battery module includes a battery module input connector configured to receive electrical power from another battery module and/or a charging unit.

In still another aspect, a method is provided for coupling a battery module to a medical support system including an implantable or wearable medical device. The battery module may include a first housing, one or more battery cells disposed within the first housing, a connector cable fixedly connected with the first housing and extending from the first housing to a distal end of the connector cable, the connector cable including electrical conductors and an optical fiber, and a battery module output connector connected to the distal end of the connector cable. The method may include electrically connecting metal pins of the battery module output connector to metal contact plates of an input connector of the medical support system so as to allow transfer of power from the one or more battery cells to the medical support system, wherein the input connector is mounted to a second housing of the medical support system, has no moving parts, and is sealed to prevent water or dust ingression into the second housing. The method may further include optically connecting the optical fiber to an optical connection of the input connector of the medical support system so as to allow transmission of data between the battery module and the medical support system. The method may further include latching the battery module output connector to the second housing of the medical device so as to physically connect the battery module to the medical support system.

In many embodiments of the method, latching the battery module output connector to the second housing comprises mechanical latching. In some embodiments, latching the battery module output connector to the second housing comprises mating dimples of two latching arms of the battery module output connector to recesses on surfaces of the second housing having complementary shapes and sizes to the dimples.

In many embodiments of the method, latching the battery module output connector to the second housing comprises magnetic latching. In some embodiments, latching the battery module output connector to the second housing comprises magnetically latching the battery module output connector to the second housing. In some embodiments, the method further includes applying a particular force to unlatch the battery module output connector from the second housing.

In many embodiments of the method, the metal pins comprise spring-loaded pins. In some embodiments, electrically connecting the metal pins to the metal contact plates comprises pressing the spring-loaded pins against the metal plates.

In many embodiments of the method, the electrical conductors include two redundant pairs of conductors arranged symmetrically on opposite sides of the optical fiber to enable coupling of the battery module output connector to the input connector in each of two opposite orientations. In some embodiments, each of the electrically connecting, optically connecting, and latching may occur in each of the two opposite orientations.

In many embodiments of the method, the medical support system includes an implantable blood pump. In some embodiments, the medical support system includes an implantable blood pump and an external controller configured to supply power to the implantable blood pump, the external controller including the second housing and the input connector.

In many embodiments of the method, the battery module includes a battery module input connector configured to receive electrical power from an additional battery module. In some embodiments, the method further includes electrically connecting the additional battery module to the battery module via the battery module input connector.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figures 1, 2:
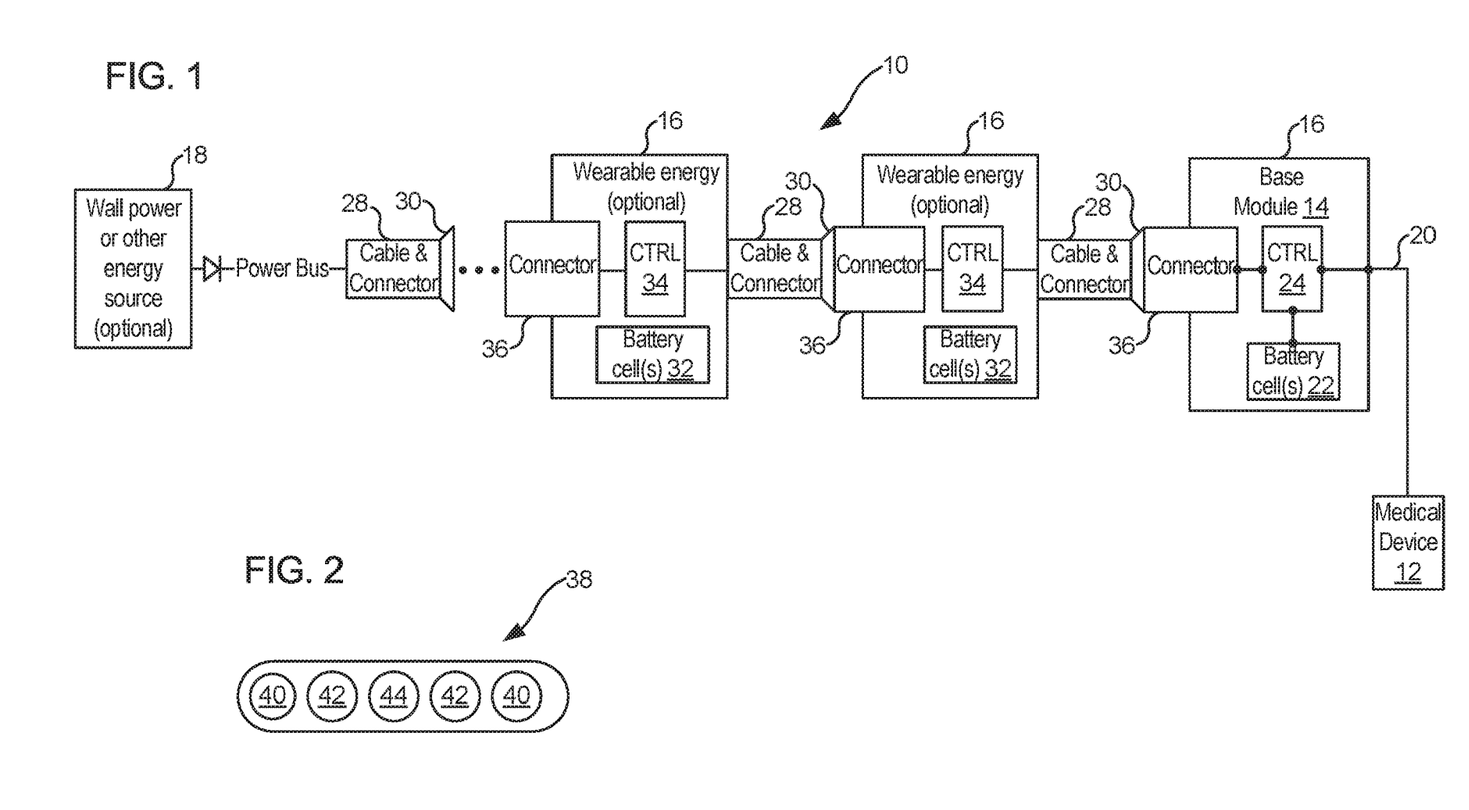
FIG. 1 is a simplified schematic diagram illustrating a system for supplying power to a medical device worn by a user or implanted in the user, in accordance with many embodiments.
FIG. 2 illustrates a cross-section of a connector, in accordance with many embodiments.

Referring now to the drawings, in which like reference numerals represent like parts throughout the several views, FIG. 1 shows a system 10, in accordance with many embodiments, for supplying power to a medical device worn by a user or implanted in the user. The system 10 includes a wearable or implantable medical device 12, a base module 14, a plurality of external battery modules 16, and a non-worn energy source 18. The external battery modules 16 are configured for selective serial connection to enable the connection of any suitable number of the external battery modules 16 to the base module 14 to vary the total battery capacity worn by the user. The non-worn energy source 18 can be any suitable energy source, for example, a wall power unit configured to convert utility power (e.g., 110 volt AC power) to direct current having a voltage level compatible with the external battery modules 16 and the base module 14. The non-worn energy source 18 can be selectively and intermittently connected to the most distal external battery module 16 to supply electrical power used to recharge the external battery modules 16, recharge the base module 14, and/or be output to the medical device 12 via a connection line 20.

The base module 14 is configured to supply operating electrical power to the medical device 12 via the connection line 20. The base module 14 includes one or more base module battery cells 22, a base module controller 24, and a base module input connector 26. The base module controller 24 is configured to supply power to the medical device 12 output by the one or more base module battery cells 22 and/or received via the base module input connector 26. In many embodiments, the base module controller 24 includes an integrated charger for recharging the one or more base module battery cells 22 via electrical power received via the base module input connector 26. In many embodiments, the base module controller 24 is configured to detect when at least one external battery module 16 or the non-worn energy source 18 is connected to the base module input connector 26. For example, the base module input connector 26 can include a data connection to receive a signal when at least one external battery module 16 or the non-worn energy source 18 is connected to the base module input connector 26. Alternatively, the base module controller 24 can be configured to detect when a suitable voltage potential is applied to the base module input connector 26 indicative of at least one external battery module 16 or the non-worn energy source 18 being connected to the base module input connector 26. When the connection of at least one of the external battery modules 16 or the non-worn energy source 18 to the base module input connector 26 is detected, the base module controller 24 can supply electrical power to the medical device solely via electrical power received via the base module input connector 26 and can simultaneously recharge the one or more base module battery cells 22 via electrical power received via the base module input connector 26 if the one or more base module battery cells 22 are not already fully charged. When the base module controller 24 does not detect the connection of any power source to the base module input connector 24, the base module controller 24 is configured to supply electrical power to the medical device 12 via electrical power from the one or more base module battery cells 22.

In the illustrated embodiment, each of the external battery modules 16 includes an output cable 28, an output connector 30, one or more external battery cells 32, an external battery controller 34, and an input connector 36. The external battery controller 34 is configured to supply power via the output connector 30 output by the one or more external battery cells 32 and/or received via the input connector 36. In many embodiments, the external battery controller 34 includes an integrated charger for recharging the one or more external battery cells 32 via electrical power received via the input connector 36. In many embodiments, the external battery controller 34 is configured to detect when at least one external battery module 16 or the non-worn energy source 18 is connected to the input connector 36. For example, the input connector 36 can include a data connection to receive a signal when at least one external battery module 16 or the non-worn energy source 18 is connected to the input connector 26. Alternatively, the external battery controller 34 can be configured to detect when a suitable voltage potential is applied to the input connector 36 indicative of at least one external battery module 16 or the non-worn energy source 18 being connected to the input connector 36. When the connection of at least one of the external battery modules 16 or the non-worn energy source 18 to the input connector 36 is detected, the external battery controller 34 can supply electrical power via the output connector 30 via electrical power received via the input connector 36 and can simultaneously recharge the one or more external battery cells 32 via electrical power received via the input connector 36 if the one or more external battery cells 32 are not already fully charged. When the external battery controller 34 does not detect the connection of any power source to the input connector 34, the external battery controller 34 is configured to output electrical power via the output connector 30 via electrical power from the one or more external battery cells 32.

Any suitable serial combination of the external battery modules 16 can be used. For example, zero, one, two, three, four, or greater of the external battery modules 16 can be serially connected to the base module 14 to supply power to the base module 14 for supply to the medical device 12. Additionally, in many embodiments, the non-worn power source 18 can be connected directly to the base module 14 to supply electrical power that can be used by the base module 14 to supply electrical power to the medical device 12 and to recharge the one or more base module battery cells 22 if the one or more base module battery cells 22 are not already fully charged. While the external battery modules 16 are configured to be serially connected physically, the external battery modules 16 are configured so as to be connected in parallel electrically so as to not vary the voltage supplied to the base module 14.

FIG. 2 shows a connector arrangement 38 that can be used in the base module input connector 26, the output connector 30, and the input connector 36. The connector arrangement 38 includes two first power connectors 40, two second power connectors 42, and a data connector 44. The first and the second connectors 40, 42 are used to transfer power. For example, each of the first connectors 40 can be electrically connected to a power lead and each of the second connectors 42 can be electrically connected to a ground lead, and vice-versa. The data connector 44 is used to connect data lines to transmit data between the base module controller 24 and the one or more external battery controllers 34 and/or between any of the one or more external battery controllers 34. The symmetrical arrangement of the connectors 40, 42, 44 accommodates connection of the connector arrangement 38 in opposite orientations, thereby accommodating proper connection in either of the two possible orientations between connectors.

Figure 3:
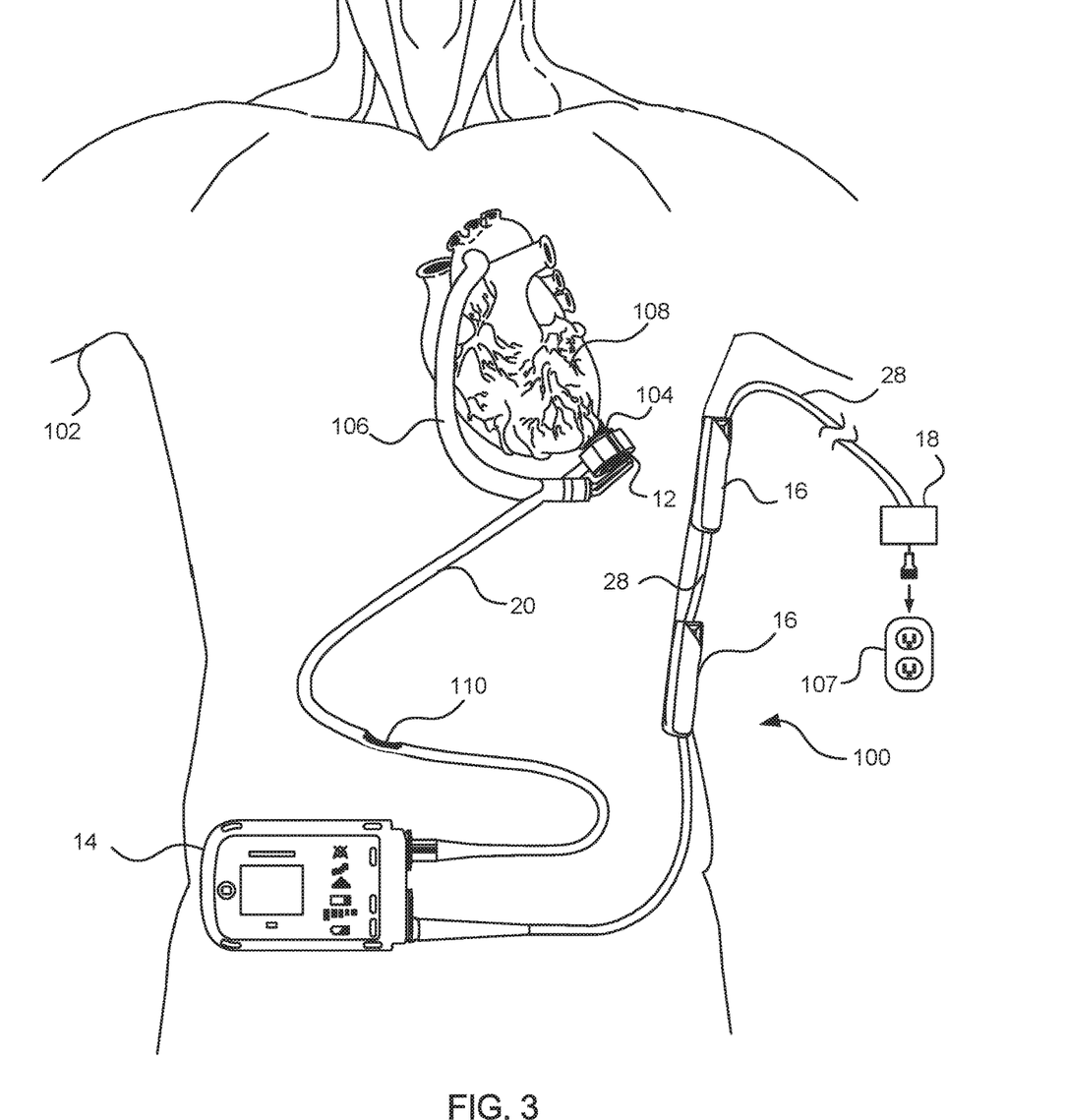
FIG. 3 illustrates an example medical device system that employs the system of FIG. 1.

The system 10 can be employed in any suitable medical system (e.g., a worn or at least partially implanted medical system). For example, FIG. 3 illustrates a mechanical circulatory support system 100 that employs the system 10. The mechanical circulatory support system 100 includes an implantable blood pump assembly (i.e., medical device 12) implanted in a patient 102, a ventricular cuff 104, an outflow cannula 106, and an external system controller (base module 14). In the illustrated configuration, two of the external battery modules 16 are shown serially connected to the external system controller 14. As described herein, however, any suitable number of the external battery modules 16 and/or the non-worn energy source 18 (e.g., that can be powered via being plugged into an outlet 107) can be coupled with the external system controller 14 to supply power to the external system controller 14 for supply to the blood pump assembly 12. The blood pump assembly 12 can include a VAD that is attached to an apex of the left ventricle, as illustrated, or the right ventricle, or both ventricles of the patient's heart 108. The VAD can include a centrifugal pump (as shown) that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. The blood pump assembly 12 can be attached to the heart 108 via the ventricular cuff 104, which can be sewn to the heart 108 and coupled to the blood pump 12. The other end of the blood pump 12 connects to the ascending aorta via the outflow cannula 106 so that the VAD effectively diverts blood from the weakened ventricle and propels it to the aorta for circulation through the rest of the patient's vascular system.

FIG. 3 illustrates the mechanical circulatory support system 100 during battery powered operation by the system 10 via the two connected external battery modules 16. A driveline (connection line 20) that exits through the patient's abdomen 110 connects the implanted blood pump assembly 12 to the external system controller 14, which monitors system 100 operation. Related controller systems applicable to the present invention are described in greater detail below and in U.S. Pat. Nos. 5,888,242, 6,991,595, 8,323,174, 8,449,444, 8,506,471, 8,597,350, and 8,657,733, EP 1812094, and U.S. Patent Publication Nos. 2005/0071001 and 2013/0314047, all of which are incorporated herein by reference for all purposes in their entirety. As described herein the power system 10 used to power the system 100 can include any suitable combination (zero, one, two, three, four, or more) of the external battery modules 16 and/or the non-worn power source 18.

Figure 4:
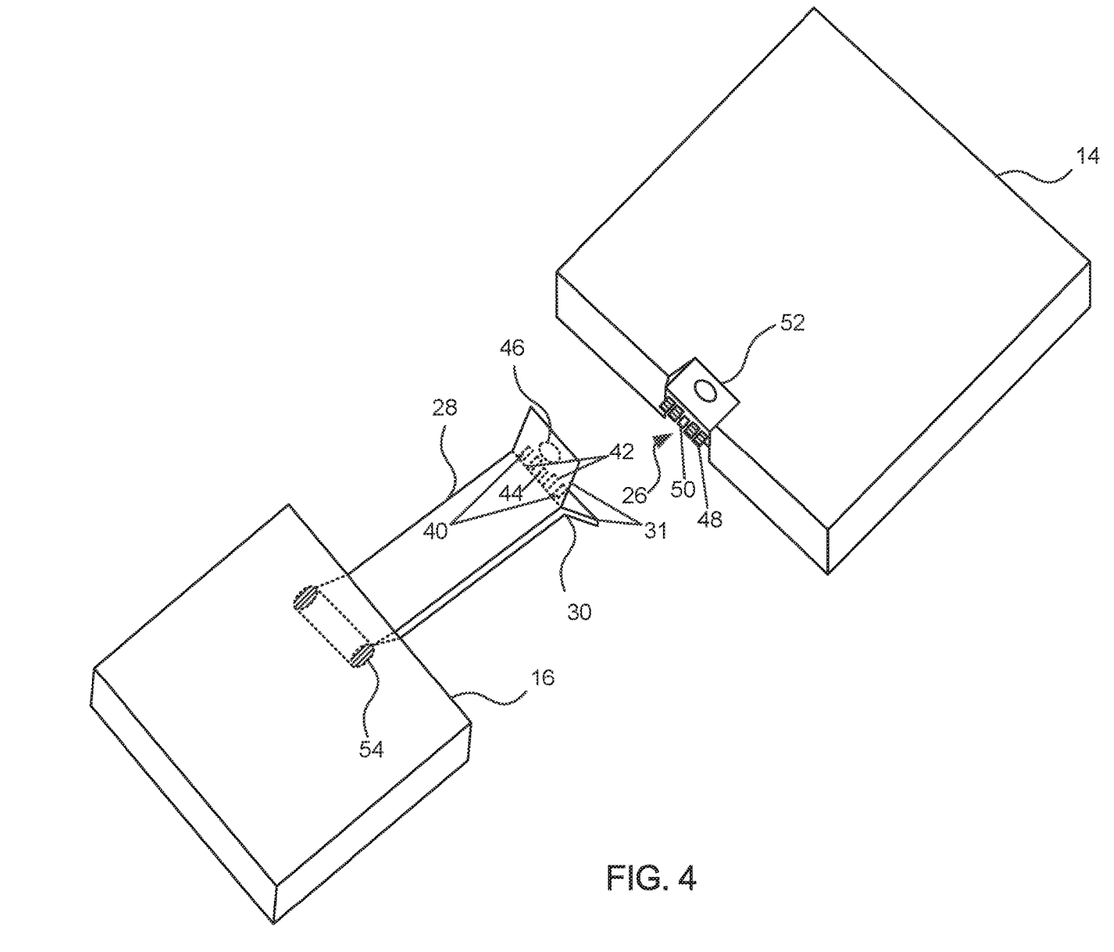
FIG. 4 illustrates a battery module that includes a connector assembly having a mechanical latching mechanism, in accordance with many embodiments.

FIG. 4 illustrates a battery module with a connector assembly, in accordance with many embodiments. Although not shown in FIG. 4, as described above with respect to FIG. 1, the battery module 16 can include one or more battery cells disposed within its housing that may provide electrical power to a medical system including an implanted or worn medical device. For example, the battery cells of the battery module 16 can provide electrical power to an external controller 14, which is configured to supply power to a medical device such as an implantable blood pump.

As shown in FIG. 4, the battery module 16 includes a connector cable 28 fixedly connected with the housing and extending from the housing to a distal end of connector cable 28. The connector cable 28 includes electrical conductors 40 and 42 configured to transfer power from the one or more battery cells and an optical fiber 44 to transfer data. The battery module 16 further includes a battery module output connector 30 connected to the distal end of the connector cable and configured to be removably coupled with an input connector 26 mounted on the external controller 14. The input connector 26 includes metal contact plates 48 that couple with exposed ends of the electrical conductors 40 and 42 and an optical connector 50 that couples with the optical fiber 44. In many presently preferred embodiments, the input connector 26 does not include any moving parts, and can be sealed to prevent water or dust ingression into the housing of the external controller 14.

The exposed ends of the electrical conductors 40 and 42 can include spring-loaded metal pins coupled to the electrical conductors. In some embodiments, the spring-loaded metal pins are of complementary shapes and sizes to the respective metal contact plates 48 of the medical device input connector 26 so as to allow electrical connection between the battery module 16 and the external controller 14. The use of spring-loaded metal pins to couple with the metal contact plates 48 may avoid damaging the pins during mating of connector cable 28 with input connector 26.

While the above-mentioned features of battery module output connector 30 and input connector 26 allow for electrical and optical coupling of electrical conductors 40, 42 and optical fiber 44 with the external controller 14 in order to transmit electrical power and data, in many embodiments the battery module 16 is physically coupled to external controller 14 so that the electrical and optical connections remain securely coupled. Accordingly, in many embodiments, the battery module output connector 30 also includes a latching mechanism 31. In some embodiments, the latching mechanism 31 includes two latching arms 31. Each of the latching arm 31 can include a dimple 46 on the outer surface of the latching arm and a corresponding protrusion on the inner surface of the latching arm. The protruding portion of each dimple 46 can have a complementary shape and size to a respective recesses 52 on the housing of external controller 14, so that latching arm 31 is configured to mate with the recess 52. In some embodiments, the recesses 52 may be sized to allow a snap fit connection with the dimples 46 of latching arms 31 Although only shown on the top surface of the housing of external controller 14, an additional recess 52 can be disposed on the bottom surface of the housing of the external controller 14 so as to mate with the bottom latching arm 31.

As described above with respect to FIG. 2, the electrical conductors 40, 42 and the optical fiber 44 can be arranged in a linear array within the connector cable 28 so that the connector cable 28 has an elongated rectangular cross section. The elongated rectangular or flat nature of the cross section may allow connector cable 28 to easily conform to a patient's body without excessive twisting and/or tangling of the cable. As also described above with respect to FIG. 2, the two pairs of electrical conductors 40, 42 can be arranged symmetrically on opposite sides of optical fiber 44 to enable coupling of the battery module output connector 30 to the input connector 26 in each of two opposite orientations.

The battery module 16 can include a spooling assembly 54 disposed within its housing, on which the connector cable can be spooled and unspooled. The spooling assembly 54 may allow a patient or other user to vary the length by which the connector cable 28 extends from the housing. In some embodiments, the spooling assembly 54 is spring loaded and configured to allow for locking of the connector cable at a desired length and to allow for selective retraction of the connector cable.

Figure 5:
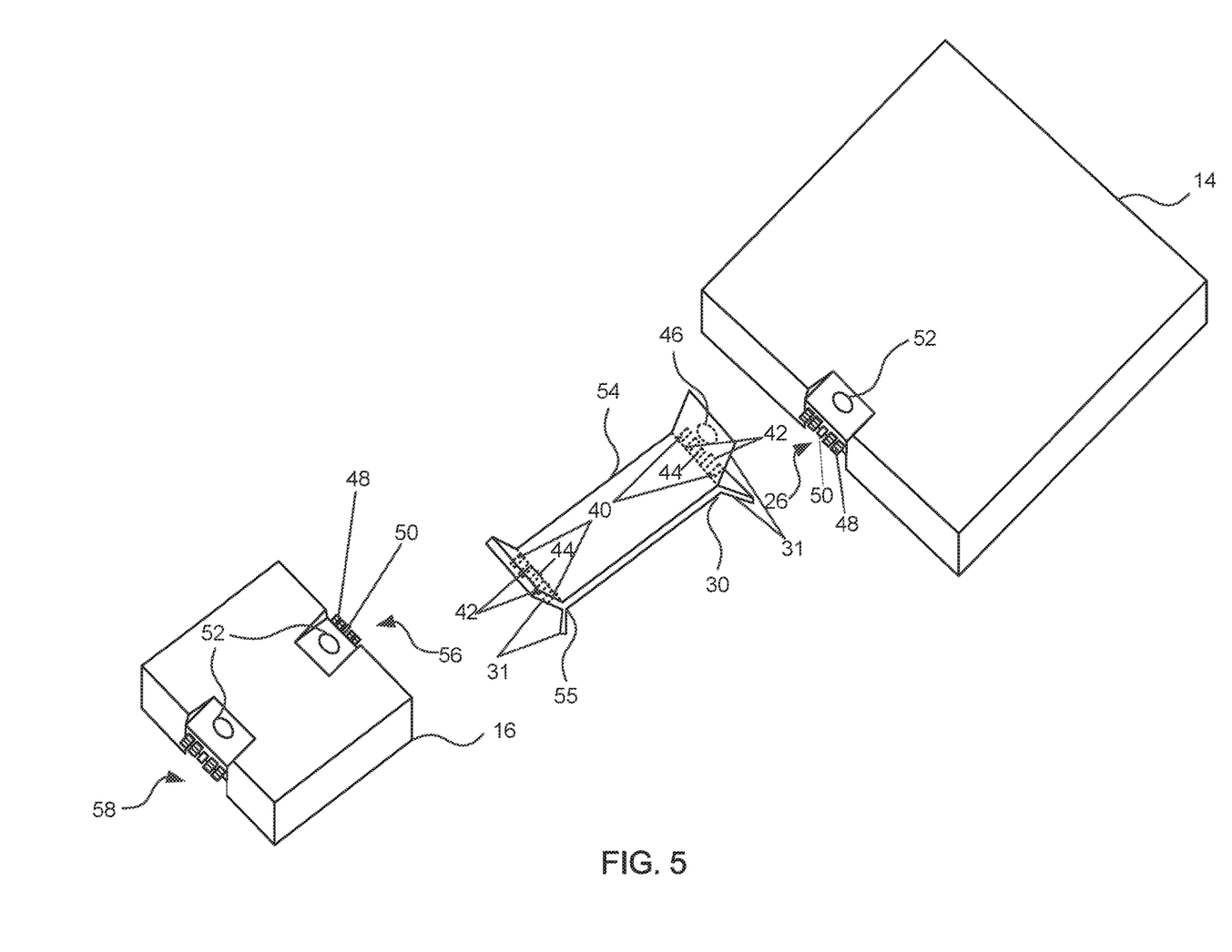
FIG. 5 illustrates a connector assembly that includes mechanical latching mechanisms, in accordance with many embodiments.

FIG. 5 illustrates a connector assembly, in accordance with many embodiments. The connector assembly includes a connector 54 that operates similarly to connector cable 28 and battery module output connector 30, except that connector 54 is decoupleable from the battery module 16. The connector 54 is a separate component that is configured to removably couple to either or both of the external controller 14 and/or the battery module 16. The connector 54 includes a first connecting end 30 similar to battery module output connector 30 described above with respect to FIG. 4. The connector 54 includes the electrical conductors 40, 42 and an optical fiber 44. The output connector 30 is configured to couple to the metal contacts 48 and optical connector 50 of input connector 26 mounted to external controller 14. As described above, the electrical conductors 40, 42 can be coupled with spring-loaded pins configured to electrically couple with the metal contacts 48. The connector 54 includes a first set of latching arms 31 with dimples 46, similar to latching arms 31 described in FIG. 4, which mechanically latch the connector 54 to the recesses 52 on the external controller 14.

At the opposite end of the first connecting end 30, the connector 54 include a second connecting end 55 for coupling with an output connector 56 of the battery module 16. Although not shown in FIG. 5, the connecting end 55 may also be used to couple the connector 54 to the external controller 14 or another external controller configured similar thereto. The output connector 56 can include metal contacts 48 and an optical connector 50 similar to the input connector 26 of the external controller 14. The second connecting end 55 can include additional spring-loaded contacts connected to the electrical conductors 40, 42 and an optical connector coupled to the optical fiber 44. As described above, the electrical conductors 40 and 42 can be connected to spring-loaded pins that allow for electrical connection between the connector 54 and the output connector 56 of the battery module 16. The second connecting end 55 can include a second pair of latching arms 31 with dimples 46 (not shown). The dimples 46 on the latching arms 31 at second connecting end 55 can be configured to latch to the recesses 52 on surfaces of the battery module 16 as described above. The recesses 52 on the battery module 16 can be the same size and shape as the recesses 52 on the external controller 14, to allow a snap fit connection with the dimples 46 of the latching arms 31.

As shown in FIG. 5, the battery module 16 can optionally include an input connector 58 for receiving electrical power from another battery module 16, a non-wearable power source 18, or any other suitable power source. As can be seen in FIG. 5, the input connector 58 can include metal contacts 48 and optical connector 50 similar to that of the output connector 56 and the input connector 26. The housing of battery module 16 can also include another pair of recesses 52 similar to previously described recesses 52. In this way, each of the input connector 58, the output connector 56, and the input connector 26 can be connected with any given connecting end of the connector 54.

As described above with respect to the connector cable 28 of FIG. 4, the body of the connector 54 can have an elongated rectangular or flat cross section that may allow connector 54 to conform with a patient's body without excessive twisting and/or tangling of the cable. As also described above with respect to FIG. 2, the two pairs of electrical conductors 40, 42 can be arranged symmetrically on opposite sides of the optical fiber 44 to enable coupling of the battery module output connector 30 to the input connector 26 in each of two opposite orientations, allowing for flexibility and ease of use in connecting and disconnecting battery modules and/or external controllers.

Figure 6:
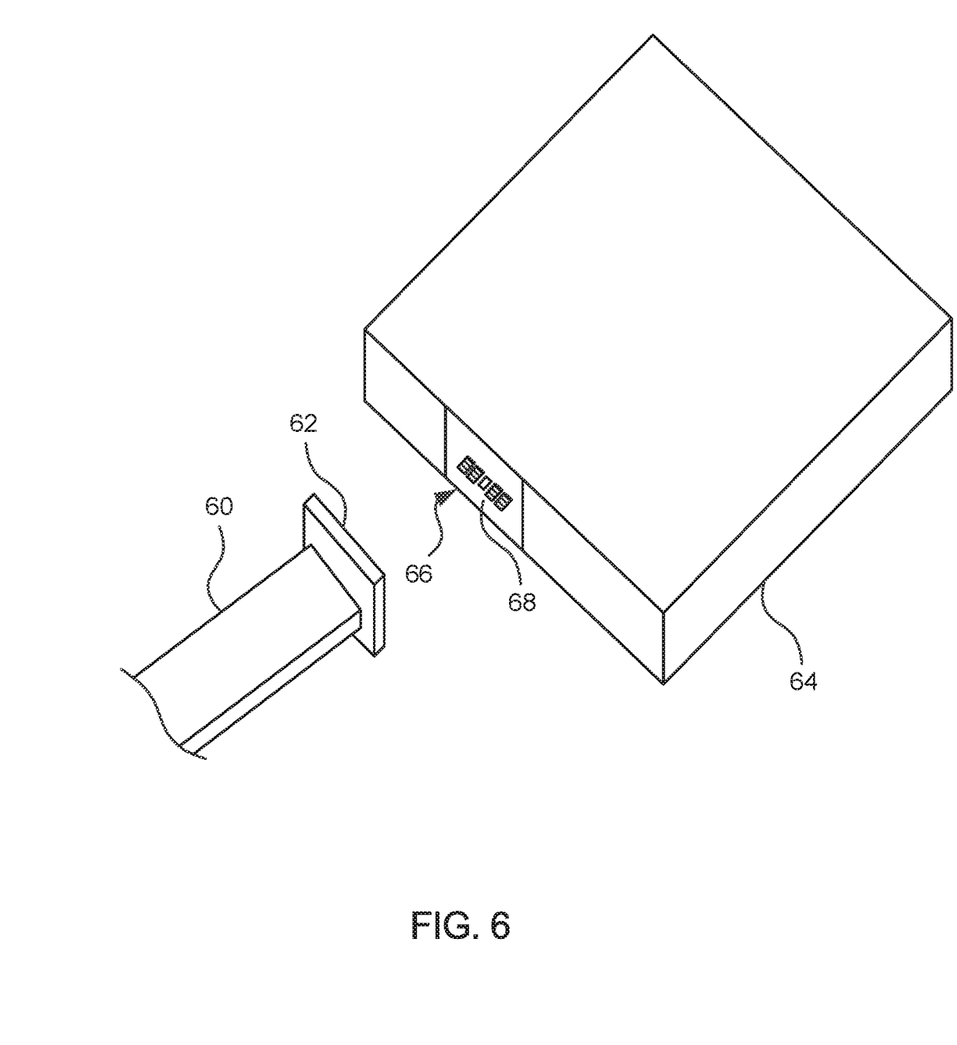
FIG. 6 illustrates a connector assembly that includes a magnetic latching mechanism, in accordance with many embodiments.

FIG. 6 illustrates a connector assembly with a magnetic latching mechanism, in accordance with many embodiments. Although not shown in detail, a connector 60 can include the components and arrangement of the connector cable 28, the output connector 30, and/or the connector 54 described above, except rather than latching arms 31, the connector 60 includes a magnetic latching mechanism. Specifically, at one or both ends of the connector 60, a first magnetic element 62 can be provided. In some embodiments, the magnet element 62 includes recesses in order to expose electrical conductors and/or optical fibers of the connector 60. In order to latch the connector 60 to the component 64 (which may be a battery, an external controller, or any other worn component in a medical device as described above), the input connector 66 can include a second magnetic element 68 that magnetically attracts the first magnetic element 62.

The first magnetic element 62 and the second magnetic element 66 can be designed to unlatch upon application of a particular breakaway force in some embodiments. In some embodiments, the particular breakaway force corresponds to a moderate pulling by the patient on the connector 60. In some presently preferred embodiments, the first magnetic element 62 and second magnetic element 66 can unlatch in response to a force resulting from a component coupled to the opposite side of the connector 60 being released from a supporting holster on the patient's body so as to avoid damage to the component 64.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A battery module for a mechanical circulatory support system, the battery module comprising:
   a housing;
   one or more battery cells disposed within the housing;
   a connector cable extending from the housing; and
   a battery module output connector connected to a distal end of the connector cable and configured to removably couple with an input connector of the mechanical circulatory support system, the connector cable including at least four connectors, the connectors being configured to transfer power from the one or more battery cells to the mechanical circulatory support system via the input connector and to transfer data between the mechanical circulatory support system and the battery module.

2. The battery module of claim 1, wherein the at least four connectors are arranged in a linear array within the connector cable so that the connector cable has an elongated rectangular cross section.

3. The battery module of claim 1, further comprising a spooling assembly on which the connector cable can be spooled and unspooled to vary a length by which the connector cable extends from the housing.

4. The battery module of claim 1, wherein the connectors comprise an optical fiber and two redundant pairs of electrical conductors arranged symmetrically on opposite sides of the optical fiber to enable coupling of the battery module output connector to the input connector in each of two opposite orientations.

5. The battery module of claim 1, wherein the battery module output connector comprises spring-loaded metal pins coupled to the at least four connectors, wherein the spring-loaded metal pins are of complementary shapes and sizes to respective metal contact plates of the input connector so as to allow electrical connection between the battery module and the mechanical circulatory support system.

6. The battery module of claim 1, wherein the battery module output connector comprises a latching mechanism configured to physically attach the battery module to a medical device housing of the mechanical circulatory support system.

7. The battery module of claim 6, wherein the latching mechanism comprises two latching arms, wherein each of the latching arms comprises a dimple of a complementary shape and size to a respective recess on a surface of the medical device housing.

8. The battery module of claim 6, wherein the latching mechanism comprises a first magnetic element configured to latch to a second magnetic element mounted to the medical device housing.

9. The battery module of claim 8, wherein the first magnetic element is configured to unlatch from the second magnetic element upon application of a particular breakaway force.

10. The battery module of claim 1, wherein the battery module comprises a battery module input connector configured to receive electrical power from another battery module and/or a charging unit.

11. The battery module of claim 1, wherein the connector cable is fixedly connected with the housing.

12. The battery module of claim 1, wherein the connector cable is decoupleable from the battery module and comprises a connecting end for coupling an output connector of the battery module.

13. A base battery module for a mechanical circulatory support system, the base battery module comprising:
  a housing;
  one or more battery cells disposed within the housing;
  a connector cable extending from the housing; and
  a battery module output connector connected to a distal end of the connector cable and configured to removably couple with an input connector of the mechanical circulatory support system, the connector cable consisting of four connectors configured to transfer power from the one or more battery cells to the mechanical circulatory support system via the input connector and to transfer data between the mechanical circulatory support system and the base battery module.

14. The base battery module of claim 13, wherein the four connectors comprise two redundant pairs of conductors arranged symmetrically to enable coupling of the battery module output connector to the input connector in each of two opposite orientations.

15. The base battery module of claim 13, wherein the four connectors are arranged in a linear array within the connector cable so that the connector cable has an elongated rectangular cross section.

16. The base battery module of claim 13, further comprising a spooling assembly on which the connector cable can be spooled and unspooled to vary a length by which the connector cable extends from the housing.

17. The base battery module of claim 13, wherein the battery module output connector comprises a latching mechanism configured to physically attach the battery module to a medical device housing of the mechanical circulatory support system.

18. The base battery module of claim 13, wherein the battery module comprises a battery module input connector configured to receive electrical power from another battery module and/or a charging unit.

19. The base battery module of claim 13, wherein the base battery module comprises an external controller.

20. The battery module of claim 1, wherein the at least four connectors comprise two redundant pairs of conductors arranged symmetrically to enable coupling of the battery module output connector to the input connector in each of two opposite orientations.

* * * * *